US012601014B2

(12) United States Patent
Jiang et al.

(10) Patent No.: US 12,601,014 B2
(45) Date of Patent: Apr. 14, 2026

(54) MULTIPLE KASP MARKER PRIMER SET FOR WHEAT PLANT HEIGHT MAJOR GENES AND USE THEREOF

(71) Applicant: JIANGSU ACADEMY OF AGRICULTURAL SCIENCES, Jiangsu (CN)

(72) Inventors: Peng Jiang, Jiangsu (CN); Xu Zhang, Jiangsu (CN); Lei Wu, Jiangsu (CN); Yi He, Jiangsu (CN); Chang Li, Jiangsu (CN)

(73) Assignee: JIANGSU ACADEMY OF AGRICULTURAL SCIENCES, Jiangsu (CN)

( * ) Notice: Subject to any disclaimer, the term of this patent is extended or adjusted under 35 U.S.C. 154(b) by 67 days.

(21) Appl. No.: 18/720,668

(22) PCT Filed: Jun. 28, 2023

(86) PCT No.: PCT/CN2023/103085
§ 371 (c)(1),
(2) Date: Jun. 17, 2024

(87) PCT Pub. No.: WO2023/232152
PCT Pub. Date: Dec. 7, 2023

(65) Prior Publication Data
US 2025/0051861 A1     Feb. 13, 2025

(30) Foreign Application Priority Data
Aug. 24, 2022    (CN) .......................... 202211020169.4

(51) Int. Cl.
*C12Q 1/6895*        (2018.01)
(52) U.S. Cl.
CPC ....... *C12Q 1/6895* (2013.01); *C12Q 2600/13* (2013.01); *C12Q 2600/156* (2013.01)
(58) Field of Classification Search
None
See application file for complete search history.

(56) References Cited

FOREIGN PATENT DOCUMENTS

| | | |
|---|---|---|
| CN | 109762812 | 5/2019 |
| CN | 110656198 | 1/2020 |
| CN | 111676312 | 9/2020 |
| CN | 114517241 | 5/2022 |
| CN | 115807119 | 3/2023 |

OTHER PUBLICATIONS

Diffenbach (PCR methods and Applications (1993) vol. 3, pp. S30-S37) (Year: 1993).*

Roux et al (PCR Methods and Applications (1995) vol. 4, pp. s185-s194) (Year: 1995).*
Peter Hedden, "The genes of the Green Revolution", Trends in Genetics, Jan. 2003, pp. 5-9, vol. 19, No. 1.
Youngjun Mo et al., "Identification and characterization of Rht25, a locus on chromosome arm 6AS affecting wheat plant height, heading time, and spike development", Theoretical and Applied Genetics, Jun. 29, 2018, pp. 1-15.
Xiuling Tian et al., "Molecular Mapping of Reduced Plant Height Gene Rht24 in Bread Wheat", Frontiers in Plant Science, Aug. 8, 2017, pp. 1-9, vol. 8, Article 1379.
Ra McIntosh et al., "Catalogue of Gene Symbols for Wheat", 12th International Wheat Genetics Symposium, Sep. 8-13, 2013, pp. 1-31.
M. Guedira et al., "Distribution of Rht Genes in Modern and Historic Winter Wheat Cultivars from the Eastern and Central USA", Crop Science, Sep. 2010, pp. 1811-1822, vol. 50.
M.H. Ellis et al., ""Perfect" markers for the Rht-B1b and Rht-D1b dwarfing genes in wheat", Theoretical and Applied Genetics, Sep. 13, 2002, pp. 1038-1042, vol. 105.
Awais Rasheed et al., "Development and validation of high-throughput KASP assays for genes underpinning key economic traits in bread wheat", 7th International Crop Science Congress, Aug. 14-19, 2016, pp. 153-154.
Jun-Chan Wang et al., "Kompetitive allele specific PCR (KASP) assays for functional genes of important trait in Yangmai series wheat cultivars (lines)", Jiangsu Journal of Agricultural Sciences, 2019, with English abstract, pp. 1271-1283, vol. 35, No. 6.
Li-Kui Xu et al., "Development of PCR-based Molecular Markers for Waxy and Powdery Mildew Resistance in Wheat", Journal of Nuclear Agricultural Sciences, 2014, with English abstract, pp. 1203-1207, vol. 28, No. 7.
Peng Jiang et al., "Phenotypic Characteristics and Related Gene Analysis of Ningmai Series Wheat Varieties", Scientia Agricultura Sinica, 2022, with English abstract, pp. 233-247, vol. 55, No. 2.
Qiang Zhou et al., "Molecular Identification of the Main Dwarfing Genes in Wheat Varieties in Sichuan", Journal of Triticeae Crops, 2015, pp. 1624-1630, vol. 35, No. 12.
Awais Rasheed et al., "Development and validation of KASP assays for genes underpinning key economic traits in bread wheat", Theoretical and Applied Genetics, Jun. 15, 2016, pp. 1-18.
Sue Porebski et al., "Modification of a CTAB DNA Extraction Protocol for Plants Containing High Polysaccharide and Polyphenol Components", Plant Molecular Biology Reporter, Mar. 1997, pp. 8-15, vol. 15, No. 1.
"International Search Report (Form PCT/ISA/210) of PCT/CN2023/103085", mailed on Sep. 10, 2023, with English translation thereof, pp. 1-6.

* cited by examiner

*Primary Examiner* — Katherine D Salmon
(74) *Attorney, Agent, or Firm* — JCIPRNET

(57)        ABSTRACT

A multiplex KASP marker primer set for a set of wheat plant height major genes, consisting of a pre-primer having a nucleotide sequence as shown in SEQ ID NO. 10, a post-primer having a nucleotide sequence as shown in SEQ ID NO. 11, and a universal primer having a nucleotide sequence as shown in SEQ ID NO. 9. The multiplex KASP marker primer set achieves the simultaneous detection of the Rht-B1 and Rht-D1 genes.

4 Claims, 4 Drawing Sheets

Specification includes a Sequence Listing.

P1F+P1R

| | Rating | Sequence | Position | Length bp | Tm °C | GC % |
|---|---|---|---|---|---|---|
| Sense | 57.2 | TGGCGCAGAAGCTGGAGC | 173 | 18 | 58.2 | 66.7 |
| AntiSense | 58.3 | TGGCGAAGCTGTCGTCGG | 256 | 18 | 57.9 | 66.7 |
| Product | 59.8 | | | 84 | 82.1 | |

P1H+P1R

| | Rating | Sequence | Position | Length bp | Tm °C | GC % |
|---|---|---|---|---|---|---|
| Sense | 51.9 | ACGTGGCGCAGAAGCTGG | 164 | 18 | 58.5 | 66.7 |
| AntiSense | 58.3 | TGGCGAAGCTGTCGTCGG | 256 | 18 | 57.9 | 66.7 |
| Product | 56.3 | | | 87 | 82.3 | |

P2F+P2R

| | Rating | Sequence | Position | Length bp | Tm °C | GC % |
|---|---|---|---|---|---|---|
| Sense | 43.8 | CGCTCGGGTACAAGGTGCG | 134 | 19 | 59.1 | 68.4 |
| AntiSense | 23.4 | CCCATGGCCATCTCCAGCTG | 209 | 20 | 58.5 | 65 |
| Product | 39 | | | 76 | 79.1 | |

P2H+P2R

| | Rating | Sequence | Position | Length bp | Tm °C | GC % |
|---|---|---|---|---|---|---|
| Sense | 43.9 | CGCTCGGGTACAAGGTGCG | 129 | 19 | 59.1 | 68.4 |
| AntiSense | 35.4 | CATGGCCATCTCGAGCTGCTC | 201 | 21 | 59.4 | 61.9 |
| Product | 42 | | | 74 | 78.5 | |

P3F+P3R

| | Rating | Sequence | Position | Length bp | Tm °C | GC % |
|---|---|---|---|---|---|---|
| Sense | 51.3 | GCTCGGGTACAAGGTGCG | 135 | 18 | 56 | 66.7 |
| AntiSense | 37.7 | CCATGGCCATCTCCAGCTA | 209 | 19 | 54.1 | 57.9 |
| Product | 51.8 | | | 74 | 77.8 | |

P3H+P3R

| | Rating | Sequence | Position | Length bp | Tm °C | GC % |
|---|---|---|---|---|---|---|
| Sense | 59.4 | GCTCGGGTACAAGGTGCG | 129 | 18 | 56 | 66.7 |
| AntiSense | 43.7 | ATGGCCATCTCGAGCTGCTA | 200 | 20 | 56.7 | 55 |
| Product | 51.3 | | | 72 | 77.3 | |

FIG. 2

SEQUENCE LISTING

```
Sequence total quantity: 17
SEQ ID NO: 1            moltype = DNA  length = 18
FEATURE                 Location/Qualifiers
source                  1..18
                        mol_type = other DNA
                        organism = synthetic construct
SEQUENCE: 1
tggcgcagaa gctggagc                                          18

SEQ ID NO: 2            moltype = DNA  length = 18
FEATURE                 Location/Qualifiers
source                  1..18
                        mol_type = other DNA
                        organism = synthetic construct
SEQUENCE: 2
acgtggcgca gaagctgg                                          18

SEQ ID NO: 3            moltype = DNA  length = 18
FEATURE                 Location/Qualifiers
source                  1..18
                        mol_type = other DNA
                        organism = synthetic construct
SEQUENCE: 3
tggcgaagct gtcgtcgg                                          18

SEQ ID NO: 4            moltype = DNA  length = 20
FEATURE                 Location/Qualifiers
source                  1..20
                        mol_type = other DNA
                        organism = synthetic construct
SEQUENCE: 4
cccatggcca tctccagctg                                        20

SEQ ID NO: 5            moltype = DNA  length = 21
FEATURE                 Location/Qualifiers
source                  1..21
                        mol_type = other DNA
                        organism = synthetic construct
SEQUENCE: 5
catggccatc tcgagctgct c                                      21

SEQ ID NO: 6            moltype = DNA  length = 19
FEATURE                 Location/Qualifiers
source                  1..19
                        mol_type = other DNA
                        organism = synthetic construct
SEQUENCE: 6
cgctcgggta caaggtgcg                                         19

SEQ ID NO: 7            moltype = DNA  length = 20
FEATURE                 Location/Qualifiers
source                  1..20
                        mol_type = other DNA
                        organism = synthetic construct
SEQUENCE: 7
cccatggcca tctccagcta                                        20

SEQ ID NO: 8            moltype = DNA  length = 20
FEATURE                 Location/Qualifiers
source                  1..20
                        mol_type = other DNA
                        organism = synthetic construct
```

-continued

```
SEQUENCE: 8
atggccatct cgagctgcta                                                     20

SEQ ID NO: 9              moltype = DNA   length = 18
FEATURE                  Location/Qualifiers
source                   1..18
                         mol_type = other DNA
                         organism = synthetic construct
SEQUENCE: 9
gctcgggtac aaggtgcg                                                       18

SEQ ID NO: 10             moltype = DNA   length = 41
FEATURE                  Location/Qualifiers
source                   1..41
                         mol_type = other DNA
                         organism = synthetic construct
SEQUENCE: 10
gaaggtgacc aagttcatgc tcccatggcc atctccagct a                            41

SEQ ID NO: 11             moltype = DNA   length = 41
FEATURE                  Location/Qualifiers
source                   1..41
                         mol_type = other DNA
                         organism = synthetic construct
SEQUENCE: 11
gaaggtcgga gtcaacggat tatggccatc tcgagctgct a                            41

SEQ ID NO: 12             moltype = DNA   length = 20
FEATURE                  Location/Qualifiers
source                   1..20
                         mol_type = other DNA
                         organism = synthetic construct
SEQUENCE: 12
cccatggcca tctccagctg                                                     20

SEQ ID NO: 13             moltype = DNA   length = 20
FEATURE                  Location/Qualifiers
source                   1..20
                         mol_type = other DNA
                         organism = synthetic construct
SEQUENCE: 13
cccatggcca tctccagcta                                                     20

SEQ ID NO: 14             moltype = DNA   length = 20
FEATURE                  Location/Qualifiers
source                   1..20
                         mol_type = other DNA
                         organism = synthetic construct
SEQUENCE: 14
tcgggtacaa ggtgcgggcg                                                     20

SEQ ID NO: 15             moltype = DNA   length = 21
FEATURE                  Location/Qualifiers
source                   1..21
                         mol_type = other DNA
                         organism = synthetic construct
SEQUENCE: 15
catggccatc tcgagctgct c                                                   21

SEQ ID NO: 16             moltype = DNA   length = 21
FEATURE                  Location/Qualifiers
source                   1..21
                         mol_type = other DNA
                         organism = synthetic construct
SEQUENCE: 16
catggccatc tcgagctgct a                                                   21

SEQ ID NO: 17             moltype = DNA   length = 19
FEATURE                  Location/Qualifiers
source                   1..19
                         mol_type = other DNA
                         organism = synthetic construct
SEQUENCE: 17
cgggtacaag gtgcgcgcc                                                      19
```

MULTIPLE KASP MARKER PRIMER SET FOR WHEAT PLANT HEIGHT MAJOR GENES AND USE THEREOF

CROSS-REFERENCE TO RELATED APPLICATION

This application is a 371 of international application of PCT application serial no. PCT/CN2023/103085, filed on Jun. 28, 2023, which claims the priority benefit of China application no. 202211020169.4 filed on Aug. 24, 2022. The entirety of each of the above mentioned patent applications is hereby incorporated by reference herein and made a part of this specification.

TECHNICAL FIELD

The present application relates to the field of wheat breeding, and in particular, to a KASP labeled primer set related to wheat plant height, and application thereof.

RELATED ART

Plant height is an important agronomic trait in wheat, which affects plant morphological structure and is closely related to field population yield. The use of dwarfing genes in wheat is an important part of the green revolution and has a profound impact on modern wheat breeding (Hedden P. The genes of the green revolution. *Trends in Genetics,* 2003, 19:5-9). Classical genetic studies have shown that wheat plant height is a complex trait controlled by multiple genes, with both major genes and minor loci present. So far, 25 Rht genes have been named (Mo Y, Vanzetti L S, Hale I, Spagnolo E J, Guidobaldi F, Al-Oboudi J, Odle N, Pearce S, Helguera M, Dubcovsky J. Identification and characterization of Rht25, a locus on chromosome arm 6AS affecting wheat plant height, heading time, and spike development. Theoretical and Applied Genetics, 2018, 131:2021-2035; Tian X, Wen W, Xie L, Fu L, Xu D, Fu C, Wang D, Chen X, Xia X, Chen Q, He Z, Cao S. Molecular mapping of reduced plant height gene Rht24 in bread wheat. *Frontiers in Plant Science,* 2017; McIntosh R A, Dubcovsky J, Rogers W J, Morris C, Xia X C. Catalogue of gene symbols for wheat: 2017 supplement). Rht-B1 and Rht-D1 genes located on chromosomes 4B and 4D are considered to be the major genes controlling the wheat plant height, and are widely distributed in domestic and foreign wheat breeding (Guedira M, Brown-Guedira G, Van Sanford D, Sneller C, Souza E, Marshall D. Distribution of Rht Genes in Modern and Historic Winter Wheat Cultivars from the Eastern and Central USA. *Crop Science,* 2010, 50:1811-1822).

Molecular marker-assisted selection breeding can be used to select target traits at the DNA level, so that not only are the results stable, but selection may also be carried out at the seedling stage; and therefore, the cost of phenotypic evaluation is lowered, and the efficiency of wheat breeding is improved. Ellis et al. successfully developed electrophoretic markers for Rht-B1 and Rht-D1, which can distinguish the dwarf types of Rht-B1b and Rht-D1b from the tall types of Rht-B1a and Rht-D1a by PCR/electrophoresis (Ellis M, Spielmeyer W, Gale K, Rebetzke G, Richards R. "Perfect" markers for the Rht-B1b and Rht-D1b dwarfing genes in wheat. *Theoretical and Applied Genetics,* 2002, 105:1038-1042); however, its screening method is inefficient, and its STS marker based on ordinary PCR amplification and electrophoresis technology detects up to 96 samples at a single time, and the daily throughput is about several hundred samples, which cannot meet the needs of large-scale breeding screening at present.

KASP (Kompetitive Allele Specific PCR) marker technology is based on the specific matching of primer end bases for SNP typing, which can accurately determine dialleles for SNP sites, and has the characteristics of low cost and high throughput. Its single amplification throughput is more than 10,000 samples, without need for electrophoretic amplification. The detection results can be directly obtained through fluorescence typing, making it particularly suitable for molecular marker detection in large number of samples, which is in line with breeding selection. It has broad application prospects in breeding. Rasheed et al. successfully developed KASP markers for Rht-B1 and Rht-D1 (RASHEED A, WEN W, GAO F, ZHAI S, JIN H, LIU J, GUO Q, ZHANG Y, DREISIGACKER S, XIA X. Development and validation of KASP assays for genes underpinning key economic traits in bread wheat. *Theoretical and Applied Genetics,* 2016, 129 (10): 1-18); and the KASP markers have been widely used in wheat material screening (Wang Junchan, Wu Xujiang, Hu Wenjing, Zhang Xiao, Zhang Yong, Gao Derong, Bie Tongde, Zhang Boqiao. Kompetitive allele specific PCR (KASP) assay for functional genes of important traits in Yangmai series wheat cultivars (lines). *Jiangsu Journal of Agricultural Sciences,* 2019, 35:1271-1283).

Multiplex PCR can identify multiple gene loci at one time in the same reaction system, which greatly saves time and reagents, thus being more suitable for large-scale screening in a breeding process (Xu Likui, Pan Binrong, Yue Gaohong, Mei Xixue, Liu Yongan, Zhang Zongchen, Zhou Zhihui. Development of PCR-based Molecular Markers for Waxy and Powdery Mildew Resistance in Wheat. *Journal of Nuclear Agricultural Sciences,* 2014, 28:1203-1207). The development of multiple molecular markers based on a KASP marker system can further improve the detection efficiency and reduce the cost. However, there are great difficulties in the selection of primers during multiple KASP development, which requires both universal primers for amplification and specific typing, so there are few multiple molecular markers based on the KASP marker system, and the identification of multiple KASP markers for Rht-B1 and Rht-D1 genes has not been reported yet.

SUMMARY OF INVENTION

In view of the above problems, the present application provides a multiple KASP labeled primer set for a set of major genes controlling wheat plant height, and application thereof, while completing the identification of Rht-B1 and Rht-D1 genes to improve the existing detection efficiency, which is more suitable for the screening requirements of large-scale breeding.

Specifically, the present application is achieved through the following technical solution:

First of all, the present application provides a multiple KASP labeled primer set for major genes controlling wheat plant height, where the primer set consists of a primer F with a nucleotide sequence as shown in SEQ ID NO. 10, a primer H with a nucleotide sequence as shown in SEQ ID NO. 11, and a universal primer R with a nucleotide sequence as shown in SEQ ID NO. 9.

Secondly, the present application provides a method for simultaneously detecting the Rht-B1 and Rht-D1 genes in wheat, which involves PCR amplification of wheat samples using the multiple KASP labeled primer set with nucleotide sequences as shown in SEQ ID NO. 1 to SEQ ID NO. 3, followed by fluorescence detection performed on the amplified products; if the fluorescence detection result is type A (blue), it indicates that the genotype of the sample wheat is Rht-B1b Rht-D1a (that is, it contains both Rht-B1b and Rht-D1a allelic variation); if the fluorescence detection result is type B (red), it indicates that the genotype of the sample wheat is Rht-B1a Rht-D1b (that is, it contains both Rht-B1a and Rht-D1b allelic variation); if the fluorescence detection result is type C (green), it indicates that the genotype of the sample wheat is Rht-B1b Rht-D1b (that is, it contains both Rht-B1b and Rht-D1b allelic variation); and if the fluorescence detection result is type D (black), it indicates that the genotype of the sample wheat is Rht-B1a Rht-D1a (that is, it contains both Rht-B1a and Rht-D1a allelic variation) or blank.

The PCR amplification refers to: a total PCR reaction system is 5 µL, including 2.5 µL of 2×KASP Master Mix, 0.07 µL of KASP Assay Mix, and 2.43 µL of wheat template DNA at a concentration of 20 ng/µL, where each 100 µL of the KASP Assay Mix includes: 12 µL of the primer F at a concentration of 100 µM, 12 µL of the primer H at a concentration of 100 µM, and 30 µL of the primer R at a concentration of 100 µM, supplemented with ddH$_2$O to 100 µL.

PCR reaction procedure: 94° C. for 15 min; 94° C. for 20 s, 61-55° C. for 1 min, with a decrease of 0.6° C. per cycle for a total of 10 cycles; 94° C. for 20 s, 55° C. for 1 min, a total of 26 cycles.

As shown in the following example, the above-mentioned KASP labeled primers are developed from a wide range of sources, such as wheat species from the wheat regions in the middle and lower reaches of the Yangtze River, the Huanghuai wheat region, the southwest wheat region, and the northern winter wheat region, as well as their hybrid offspring. Therefore, the KASP labeled primer set is suitable for all varieties of wheat.

Compared with the existing PCR/electrophoresis detection method, the detection method provided by an example of the present application adopts a multiple KASP technology, the disclosed KASP labeled primer set includes 2 forward specific primers and 1 reverse universal primer, and the 2 forward specific primers may be specifically bound to a target sequence for amplification, thereby realizing genotyping. The simultaneous identification of Rht-B1 and Rht-D1 genes is completed in a single PCR reaction at the same time. Compared with ordinary KASP marker detection, the detection method doubles the efficiency, halves the cost, and greatly improves the breeding efficiency, thus having broad application prospects.

BRIEF DESCRIPTION OF DRAWINGS

FIG. 2 shows primer evaluation results.

DESCRIPTION OF EMBODIMENTS

Figure 1:
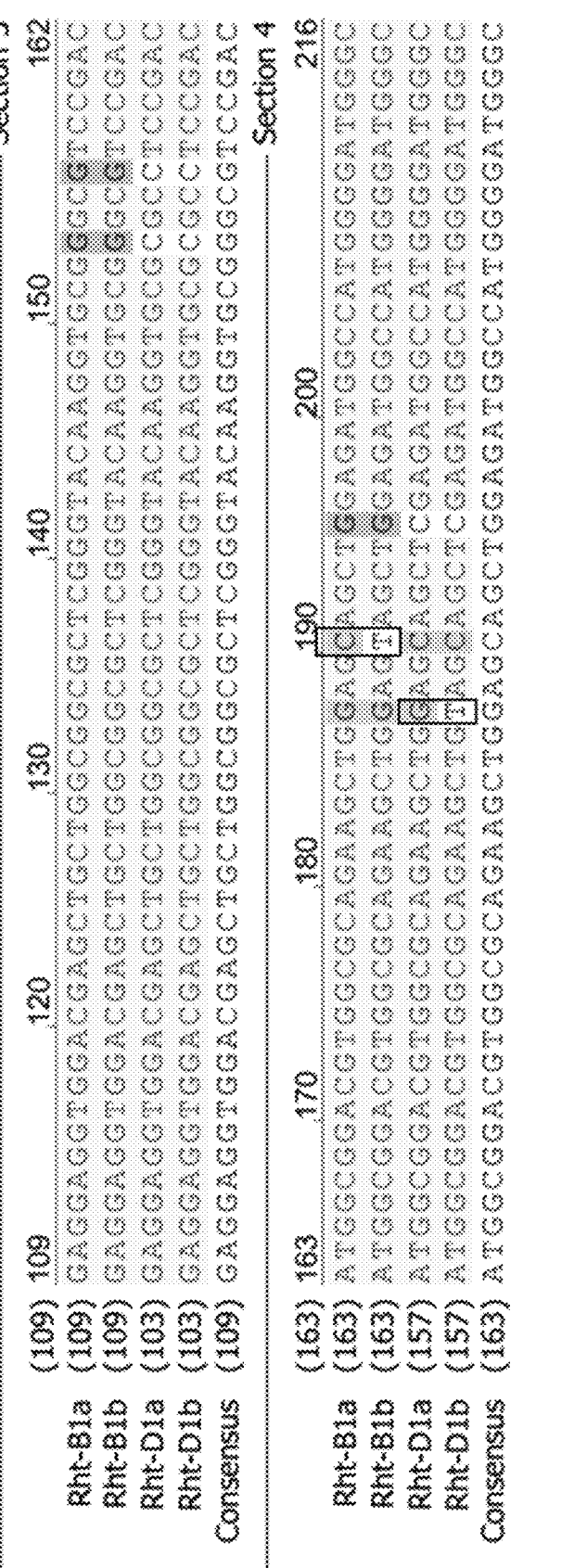
FIG. 1 is a schematic diagram of differential SNPs.

Sources of test materials involved in the following Examples:

The materials of 22 wheat varieties including Ningmai 9 (Rht-B1b Rht-D1a), Mianmai 37 (Rht-B1a Rht-D1b) and Yangmai 5 (Rht-B1a Rht-D1a) were all conventional wheat varieties (as disclosed in the following documents: Jiang Peng, Zhang Peng, Yao Jinbao, Wu Lei, He Yi, Li Chang, Ma Hongxiang, Zhang Xu. Phenotypic Characteristics and Related Gene Analysis of Ningmai Series Wheat Varieties. *SCIENTIA AGRICULTURA SINICA,* 2022, 55:233-247; Wang Junchan, Wu Xujiang, Hu Wenjing, Zhang Xiao, Zhang Yong, Gao Derong, Bie Tongde, Zhang Boqiao. Kompetitive allele specific PCR (KASP) assay for functional genes of important traits in Yangmai series wheat cultivars (lines). *Jiangsu Journal of Agricultural Sciences,* 2019, 35:1271-1283; Zhou Qiang, Yuan Zhongwei, Ou Junmei, Ren Yong, Du Xiaoying, Tao Jun, Li Shengrong, Liu Dengcai. Molecular Identification of the Main Dwarfing Genes in Wheat Varieties in Sichuan. *Journal of Triticeae Crops,* 2015, 35 (12): 1624-1630). The specific wheat names involved in the Examples are shown in Table 1, with some material settings being duplicated. 360 high-generation lines were derived from the field selection nursery (generation F5) of the Academy of Agricultural Sciences. These materials were all obtained by hybridizing using existing bred varieties or lines, and by continuous multi-generation field selection. The sources are detailed in Table 4. All materials in the following Examples were preserved and provided by the wheat genetics and 10 breeding team of Jiangsu Academy of Agricultural Sciences.

TABLE 1

Biological material information

| Number | Name | P3 | Rht-B1 | Rht-D1 |
|---|---|---|---|---|
| 1 | Mianmai 37 | B (Rht-B1a/Rht-D1b) | Rht-B1a | Rht-D1b |
| 2 | Yangmai 5 | D (Rht-B1a/Rht-D1a) | Rht-B1a | Rht-D1a |
| 3 | amada | D (Rht-B1a/Rht-D1a) | Rht-B1a | Rht-D1a |
| 4 | Yangmai 6 | A (Rht-B1b/Rht-D1a) | Rht-B1b | Rht-D1a |
| 5 | amada | D (Rht-B1a/Rht-D1a) | Rht-B1a | Rht-D1a |
| 6 | Yangmai 158 | A (Rht-B1b/Rht-D1a) | Rht-B1b | Rht-D1a |
| 7 | Ningmai 8 | A (Rht-B1b/Rht-D1a) | Rht-B1b | Rht-D1a |
| 8 | Yangmai 158 | A (Rht-B1b/Rht-D1a) | Rht-B1b | Rht-D1a |
| 9 | Ningmai 9 | A (Rht-B1b/Rht-D1a) | Rht-B1b | Rht-D1a |
| 10 | Ningmai 8 | A (Rht-B1b/Rht-D1a) | Rht-B1b | Rht-D1a |
| 11 | Ningmai 9 | A (Rht-B1b/Rht-D1a) | Rht-B1b | Rht-D1a |
| 12 | Yangmai 11 | A (Rht-B1b/Rht-D1a) | Rht-B1b | Rht-D1a |
| 13 | Yangmai 16 | A (Rht-B1b/Rht-D1a) | Rht-B1b | Rht-D1a |
| 14 | Shengxuan 6 | A (Rht-B1b/Rht-D1a) | Rht-B1b | Rht-D1a |
| 15 | Yangmai 18 | A (Rht-B1b/Rht-D1a) | Rht-B1b | Rht-D1a |
| 16 | Jingshuang16 | D (Rht-B1a/Rht-D1a) | Rht-B1a | Rht-D1a |
| 17 | Emai 16 | D (Rht-B1a/Rht-D1a) | Rht-B1a | Rht-D1a |
| 18 | Yangmai 22 | A (Rht-B1b/Rht-D1a) | Rht-B1b | Rht-D1a |
| 19 | Emai 23 | A (Rht-B1b/Rht-D1a) | Rht-B1b | Rht-D1a |
| 20 | Yangmai 22 | A (Rht-B1b/Rht-D1a) | Rht-B1b | Rht-D1a |
| 21 | Yangmai 16 | A (Rht-B1b/Rht-D1a) | Rht-B1b | Rht-D1a |
| 22 | Huaimai 33 | B (Rht-B1a/Rht-D1b) | Rht-B1a | Rht-D1b |
| 23 | Bainong 3217 | D (Rht-B1a/Rht-D1a) | Rht-B1a | Rht-D1a |
| 24 | P59 | C (Rht-B1b/Rht-D1b) | Rht-B1b | Rht-D1b |
| 25 | Huaimai 705 | B (Rht-B1a/Rht-D1b) | Rht-B1a | Rht-D1b |
| 26 | Yang 14-214 | A (Rht-B1b/Rht-D1a) | Rht-B1b | Rht-D1a |
| 27 | Ningmai 23 | A (Rht-B1b/Rht-D1a) | Rht-B1b | Rht-D1a |
| 28 | Emai 15 | D (Rht-B1a/Rht-D1a) | Rht-B1a | Rht-D1a |

The seeds of all test materials in Table 1 were germinated at room temperature for about 7 days, young leaves are cut off, and genomic DNA was extracted by the conventional CTAB method. The specific steps were as follows:

(1) The young leaves were placed in a 2 mL centrifuge tube, with two 2.5 mm sterilized steel balls being added, and frozen in liquid nitrogen, and the leaves were crushed using a tissue grinder.

(2) 700 µL of CTAB extraction buffer was added into the product, and the obtained mixture was placed in a water bath at 65° C. for 20 min, during which the mixture was evenly mixed upside down several times every 5 min.

(3) 700 µL of chloroform:isoamyl alcohol (24:1) was added, the product was evenly mixed upside down and centrifuged at 13,000 rpm for 10 min, and 600 µL of supernatant was pipetted and transferred to a new 2 mL centrifuge tube.

(4) An equal volume of chloroform:isoamyl alcohol (24: 1) was added, the product was evenly mixed upside down and centrifuged at 13,000 rpm for 10 min, and 300 µL of supernatant was pipetted and transferred to a new 1.5 mL centrifuge tube.

(5) 600 µL of anhydrous ethanol was added, and the obtained mixture was mixed well and then placed at −20° C. for 30 min.

(6) The obtained product was centrifuged at 13,000 rpm for 10 min, with supernatant being discarded, and washed and precipitated with 150 µL of 75% ethanol.

(7) The product was dried with a vacuum dryer for about 40 min, water was added for dissolving DNA, so as to obtain template DNA.

(This extraction method is a conventional method, and the extraction method adopted in this Example can be found in the document "Porebski S, Bailey L, Baum B. Modification of CTAB DNA Extraction Protocol for Plants Containing High Polysaccharide and Polyphenol Components. *Plant Molecular Biology Reporter,* 1997, 15:8-15").

The diagnostic markers for major genes Rht-B1 and Rht-D1 controlling plant height were synthesized according to the conventional methods based on reports by RASHEED et al. (see the document "RASHEED A, WEN W, GAO F, ZHAI S, JIN H, LIU J, GUO Q, ZHANG Y, DREISIGACKER S, XIA X. Development and validation of KASP assays for genes underpinning key economic traits in bread wheat. *Theoretical and Applied Genetics,* 2016, 129 (10): 1-18").

The gene sequences of Rht-B1a (FR668586.2), Rht-B1b (FN649763.1), Rht-D1a (AJ242531.1) and Rht-D1b (JF930281.1) were obtained from the website NCBI (their gene sequences may also be found in the content published in the document "(Ellis M, Spielmeyer W, Gale K, Rebetzke G, Richards R. "Perfect" markers for the Rht-B1b and Rht-D1b dwarfing genes in wheat. *Theoretical and Applied Genetics,* 2002, 105:1038-1042)"). Through sequence alignment, sequences of about 20 bp in length were artificially selected at the differential SNPs as specific primers, a sequence of about 20 bp in length was selected in a homologous sequence region as a universal primer, and finally, Primer 6.0 software was used to evaluate the artificially designed primers.

The obtained primers are shown in Table 2. A KASP marker system includes two specific primers (F/H) and one universal primer (R). In the case of fluorescence detection, a specific sequence GAAGGTGACCAAGTTCATGCT capable of fluorescently binding to FAM was added to the 5' end of the primer F shown in Table 2, and a specific sequence GAAGGTCGGAGTCAACGGATT capable of fluorescently binding to HEX was added to the 5' end of the primer H shown in Table 2. These primer sequences were synthesized by Sangon Biotech (Shanghai) Co., Ltd.

A total KASP (PCR) reaction system was 5 µL, including 2.5 µL of 2×KASP Master Mix (LGC Biosearch Technologies), 0.07 µL of KASP Assay Mix, and 2.43 µL of template DNA at a concentration of 20 ng/µL, where each 100 µL of the KASP Assay Mix includes: 12 µL of the primer F at a concentration of 100 µM, 12 µL of the primer H at a concentration of 100 µM, and 30 µL of the primer R at a concentration of 100 µM, supplemented with ddH₂O to make up the balance.

6

KASP Assay Mix KASP (PCR) reaction procedure: 94° C. for 15 min; 94° C. for 20 s, 61-55° C. for 1 min, with a decrease of 0.6° C. per cycle for a total of 10 cycles; 94° C. for 20 s, 55° C. for 1 min, a total of 26 cycles. The PCR results were scanned and analyzed by a KASP fluorescence analyzer (with model of PHERAstar plus from LGC).

Example 1 Development and Validation of Multiple KASP Markers for Rht-B1 and Rht-D1

1. Development of Multiple KASP Markers for Rht-B1 and Rht-D1

An AlignX function module of Vector NTI software was used for sequence alignment of Rht-B1a, Rht-B1b, Rht-D1a and Rht-D1b. There was a C/T base difference between Rht-B1a and Rht-B1b at 190 bp, and there was a G/T base difference between Rht-D1a and Rht-D1b at 181 bp (FIG. 1), which were relatively close. Primers were designed for the two SNP differences. Through multiple rounds of sequence position and length adjustment, Primer 6.0 software was used for primer evaluation (the evaluation results are as shown in FIG. 2), and three sets of primers P1, P2, and P3 were ultimately determined (Table 2).

TABLE 2

Primer sequences of KASP

| | F | H | universal primer R |
|---|---|---|---|
| P1 | TGGCGCAGAAGCTG GAGC (SEQ ID NO. 1) | ACGTGGCGCAGAAG CTGG (SEQ ID NO. 2) | TGGCGAAGCTGTCG TCGG (SEQ ID NO. 3) |
| P2 | CCCATGGCCATCTC CAGCTG (SEQ ID NO. 4) | CATGGCCATCTCGA GCTGCTC (SEQ ID NO. 5) | CGCTCGGGTACAAG GTGCG (SEQ ID NO. 6) |
| P3 | CCCATGGCCATCTC CAGCTA (SEQ ID NO. 7) | ATGGCCATCTCGAG CTGCTA (SEQ ID NO. 8) | GCTCGGGTACAAGG TGCG (SEQ ID NO. 9) |

The 22 materials randomly selected in Table 1 (some of which were set to duplicate) were genotyped using the three newly developed markers (P1, P2, P3) in Table 2, that is, PCR amplification was performed using the primers labeled P1, P2, and P3, respectively, and then a KASP fluorescence analyzer (with model of PHERAstar plus from LGC) was used to scan and analyze the PCR results.

PCR reaction system (5 µL): 2.5 pL of 2×KASP Master Mix (LGC Biosearch Technologies), 0.07 µL of KASP Assay Mix, 2.43 µL of wheat template DNA at a concentration of 20 ng/µL; and PCR reaction procedure: 94° C. for 15 min; 94° C. for 20 s, 61-55° C. for 1 min, with a decrease of 0.6° C. per cycle for a total of 10 cycles; 94° C. for 20 s, 55° C. for 1 min, a total of 26 cycles.

A preparation method of KASP Assay Mix labeled P1 was as follows: each 100 µL of KASP Assay Mix included: 12 µL of the primer P1F at a concentration of 100 µM, 12 µL of the primer P1H at a concentration of 100 µM, and 30 µL of the primer P1R at a concentration of 100 µM, supplemented with ddH₂O to make up the balance.

A preparation method of KASP Assay Mix labeled P2 was as follows: each 100 µL of KASP Assay Mix included: 12 µL of the primer P2F at a concentration of 100 µM, 12 µL of the primer P2H at a concentration of 100 µM, and 30 µL of the primer P2R at a concentration of 100 µM, supplemented with ddH₂O to make up the balance.

A preparation method of KASP Assay Mix labeled P3 was as follows: each 100 µL of KASP Assay Mix included: 12 µL of the primer P3F at a concentration of 100 µM, 12 µL of the primer P3H at a concentration of 100 µM, and 30 µL of the primer P3R at a concentration of 100 µM, supplemented with ddH₂O to make up the balance.

2. Validation of Multiple KASP Markers for Rht-B1 and Rht-D1

TABLE 3

| Primer sequences of control group | | | |
| --- | --- | --- | --- |
| | F | H | universal primer R |
| Rht-B1 | CCCATGGCCATCTCCCCCATGGCCATCTCCTCGGGTACAAGGTGC AGCTG (SEQ ID NO. 12) | AGCTA (SEQ ID NO. 13) | GGGCG (SEQ ID NO. 14) |
| Rht-D1 | CATGGCCATCTCGAGCATGGCCATCTCGAGCGGGTACAAGGTGCG CTGCTC (SEQ ID NO. 15) | CTGCTA (SEQ ID NO. 16) | CGCC (SEQ ID NO. 17) |

Meanwhile, the diagnostic markers of Rht-B1 and Rht-D1 were used as a control group (their primer sequences are shown in Table 3) to detect the above 22 materials (for the primer sequences in Table 3, refer to the disclosure in the document "RASHEED A, WEN W, GAO F, ZHAI S, JIN H, LIU J, GUO Q, ZHANG Y, DREISIGACKER S, XIA X. Development and validation of KASP assays for genes underpinning key economic traits in bread wheat. *Theoretical and Applied Genetics*, 2016, 129(10):1-18"). The fluorescence detection results are shown in FIG. 3.

Figure 3:
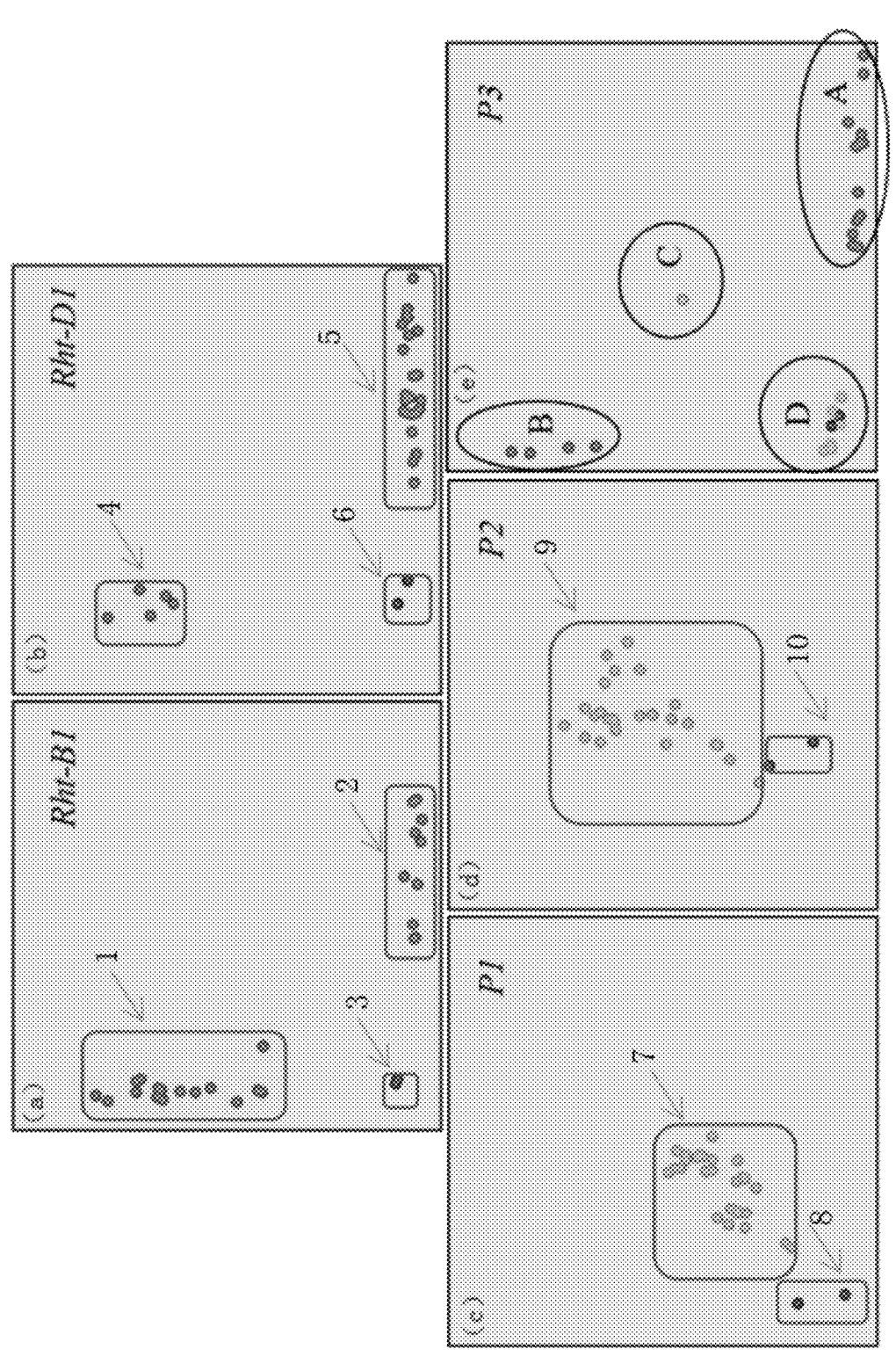
FIG. 3 shows detection results of diagnostic markers and multiple KASP markers P1, P2 and P3.

As shown in (a) of FIG. 3, the diagnostic marker of Rht-B1 distinguishes the two alleles Rht-B1a and Rht-B1b (in the figure, 1 represents that the detection result is red, which is the gene Rht-B1b; 2 represents that the detection result is blue, which is the gene Rht-B1a; 3 represents that the detection result is black, which is the blank control); and as shown in (b) of FIG. 3, the diagnostic marker of Rht-D1 distinguishes the two alleles Rht-D1a and Rht-D1b (in the figure, 5 represents that the detection result is blue, which is the gene Rht-D1a, 4 represents that the detection result is red, which is the gene Rht-D1b, and 6 represents that the detection result is black, which is the blank control).

In FIG. 3, (c), (d), and (e) are the typing results for P1, P2, and P3, respectively. (c) shows the typing result of P1. In the figure, 7 represents that the detection result is green, which is the non-blank sample detection result, and 8 represents that the detection result is black, which is the blank control. (d) shows the typing result of P2. In the figure, 9 represents that the detection result is green, which is the non-blank sample detection result, and 10 represents that the detection result is black, which is the blank control. It can be seen that all materials of P1 and P2 were amplified into one group, and their typing was not successfully completed. (e) shows the typing result of P3, which shows that the typing was successfully completed: in the figure, type A (Rht-B1b Rht-D1a, blue), type B (Rht-B1a Rht-D1b, red), type C (Rht-B1b Rht-D1b, green), and type D (Rht-B1a Rht-D1a and blank, black). The detection results in FIG. 3 are listed in Table 1. Ningmai 8, Ningmai 9, and the like are of type A, Mianmai 37, Huaimai 33, and the like are of type B, P59 is of type C, and Yangmai 5, amada, and the like are of type D. Different repeated detection results for the same material are consistent, indicating that the multiple KASP labeled P3 can replace the diagnostic markers of Rht-B1a and Rht-B1b.

In this experiment, the nucleotide sequences of fluorescent sequence-containing primer F', primer H' and universal primer R actually used in group P3 are as shown in SEQ ID NO. 10 (GAAGGTGACCAAGTTCATGCTCCCATGGC-CATCTCCAGCTA), SEQ ID NO. 11 (GAAGGTCG-GAGTCAACGGATTATGGCCATCTCGAGCTGCTA), and SEQ ID NO. 9, respectively.

Example 2 Application of Multiple KASP Labeled P3

Multiple KASP labeled P3 was used to quickly identify 360 high-generation lines. The sources of these 360 samples of wheat are described in Table 4, and the detection results are shown in Table 4 and FIG. 4. The PCR amplification system, PCR amplification procedure, and fluorescence detection method used in this Example are the same as those in Example 1. The nucleotide sequences of a primer set in PCR detection are as shown in SEQ ID NO. 10, SEQ ID NO. 11, and SEQ ID NO. 9.

TABLE 4

| Typing results of wheat materials | | |
| --- | --- | --- |
| Number | Combination (generation F5) | genotype |
| Line 001 | Ningmai 13/Yangmai 158 | A |
| Line 002 | Ningmai 13/Yangmai 158 | A |
| Line 003 | Ningmai 13/Yangmai 158 | A |
| Line 004 | Ningmai 13/Yangmai 158 | A |
| Line 005 | Ningmai 13/Yangmai 158 | A |
| Line 006 | Ningmai 13/Zhen 10216 | A |
| Line 007 | Ningmai 13/Zhen 10216 | A |
| Line 008 | Ningmai 13/Zhen 10216 | A |
| Line 009 | Ningmai 13/Zhen 10216 | A |
| Line 010 | Ningmai 13/Zhen 10216 | A |
| Line 011 | Ningmai 13/Zhen 10216 | A |
| Line 012 | Ningmai 13/Zhen 10216 | A |
| Line 013 | Ningmai 13/Zhen 10216 | A |
| Line 014 | Ningmai 13/Zhen 10216 | A |
| Line 015 | Ningmai 13/Zhen 10216 | A |
| Line 016 | Ningmai 13/Zhen 10216 | A |
| Line 017 | Ningmai 13/Ning 09-118 | A |
| Line 018 | Ningmai 13/Ning 09-118 | A |
| Line 019 | Ningmai 13/Ning 09-118 | A |
| Line 020 | Ningmai 13/Ning 09-118 | A |
| Line 021 | Ningmai 13/Ning 09-118 | A |
| Line 022 | Ningmai 13/Ning 09-118 | A |
| Line 023 | Ningmai 13/Ning 09-118 | A |
| Line 024 | Ningmai 14/Nongfeng 88 | A |
| Line 025 | Ning 9 Da 41/Yangmai 9 | A |
| Line 026 | Yangmai20/Ning 9 Da 41 | A |
| Line 027 | Yangmai20/Ning 9 Da 41 | A |
| Line 028 | Yangfumai 5/Zhen 10216 | A |
| Line 029 | Yangfumai 5/Zhen 10216 | A |
| Line 030 | Yangfumai 5/Zhen 10216 | A |
| Line 031 | Ning 12059/Zhenmai 168 | A |
| Line 032 | Longmai 28/Nongfeng 88 | A |
| Line 033 | Longmai 28/Nongfeng 88 | A |
| Line 034 | Longmai 28/Nongfeng 88 | A |
| Line 035 | Longmai 28/Nongfeng 88 | A |
| Line 036 | Longmai 28/Nongfeng 88 | A |
| Line 037 | Longmai 28/Nongfeng 88 | A |
| Line 038 | Longmai 28/Nongfeng 88 | A |
| Line 039 | Ningmai 13/Ning 11085//Zhenmai 168 | A |
| Line 040 | Ningmai 13/Ning 11085//Zhenmai 168 | A |
| Line 041 | Ningmai 13/Ning 11085//Zhenmai 168 | A |
| Line 042 | Ningmai 13/Ning 11085//Zhenmai 168 | A |
| Line 043 | Ningmai 13/Ning 11085//Zhenmai 168 | D |
| Line 044 | Ningmai 13/Ning 11085//Zhenmai 168 | A |
| Line 045 | Ningmai 13/Ning 11085//Zhenmai 168 | A |
| Line 046 | Ningmai 13/Ning 11085//Zhenmai 168 | A |
| Line 047 | Ningmai 13/Ning 11085//Zhenmai 168 | A |
| Line 048 | BC5F2 | B |
| Line 049 | BC5F2 | D |
| Line 050 | Ningmai 13/Zhen 10216 | A |

TABLE 4-continued

Typing results of wheat materials

| Number | Combination (generation F5) | genotype |
|---|---|---|
| Line 051 | Ningmai 13/Zhen 10216 | A |
| Line 052 | Ningmai 13/Zhen 10216 | A |
| Line 053 | Ningmai 13/Ning 09-118 | A |
| Line 054 | Ningmai 13/Ning 09-118 | A |
| Line 055 | Ningmai 13/Ning 09-118 | A |
| Line 056 | Ningmai 13/Ning 09-118 | A |
| Line 057 | Ningmai 13/Ning 09-118 | A |
| Line 058 | Zhenmai 168/Yangmai 9 | A |
| Line 059 | Ning 12059/Zhenmai 168 | A |
| Line 060 | Longmai 28/Nongfeng 88 | A |
| Line 061 | Longmai 28/Nongfeng 88 | A |
| Line 062 | Longmai 28/Nongfeng 88 | A |
| Line 063 | Ning 26/Nannong 9918 | A |
| Line 064 | Ning 26/Nannong 9918 | A |
| Line 065 | Ning 26/Nannong 9918 | A |
| Line 066 | Ning 26/Nannong 9918 | A |
| Line 067 | Ningmai 13 × Ning 14270 | A |
| Line 068 | Ningmai 13 × Ning 14270 | A |
| Line 069 | Ningmai 13 × Ning 14270 | A |
| Line 070 | Ningmai 13 × Ning 14270 | A |
| Line 071 | Ningmai 13 × Ning 14270 | A |
| Line 072 | Ningmai 13 × Ning 14270 | A |
| Line 073 | Ningmai 13 × Ning 14270 | A |
| Line 074 | Ningmai 13 × Ning 14270 | A |
| Line 075 | Ningmai 13 × Ning 14270 | A |
| Line 076 | Ningmai 13 × Ning 14270 | A |
| Line 077 | Ningmai 13 × Ning 14270 | A |
| Line 078 | Ningmai 13 × Ning 14270 | A |
| Line 079 | Ningmai 13 × Yangmai 9 | A |
| Line 080 | Ningmai 13 × Yangmai 9 | D |
| Line 081 | Ningmai 13 × Yang 11-125 | A |
| Line 082 | Ningmai 13 × Yang 11-125 | A |
| Line 083 | Ningmai 13 × Yang 11-125 | A |
| Line 084 | Ningmai 13 × Yang 11-125 | A |
| Line 085 | Ningmai 13 × Yangfumai 5056 | A |
| Line 086 | Ningmai 13 × Yangfumai 5056 | A |
| Line 087 | Ningmai 13 × Yangfumai 5056 | A |
| Line 088 | Ningmai 13 × Yangfumai 5056 | A |
| Line 089 | Ningmai 13 × Yangfumai 5056 | A |
| Line 090 | Ningmai 13 × Yangfumai 5056 | A |
| Line 091 | Ningmai 13 × Yangfumai 5056 | D |
| Line 092 | Ningmai 13 × Yangfumai 5056 | A |
| Line 093 | Ningmai 13 × Yangfumai 5056 | A |
| Line 094 | Ningmai 13 × Yangfumai 5056 | A |
| Line 095 | Ningmai 13 × Yangfumai 5056 | A |
| Line 096 | Ningmai 13 × Yangfumai 5056 | A |
| Line 097 | Ningmai 14 × Yangmai 23 | A |
| Line 098 | Ningmai 14 × Yangmai 23 | A |
| Line 099 | Ningmai 14 × Yangmai 23 | A |
| Line 100 | Ningmai 14 × Yangmai 23 | A |
| Line 101 | Ningmai 14 × Yangmai 23 | A |
| Line 102 | Ningmai 14 × Yangmai 23 | A |
| Line 103 | Ningmai 14 × Yangmai 23 | A |
| Line 104 | Ningmai 14 × Yang 12G16 | A |
| Line 105 | Ningmai 14 × Yang 12G16 | A |
| Line 106 | Ningmai 14 × Yang 12G16 | A |
| Line 107 | Ningmai 14 × Yang 12G16 | A |
| Line 108 | Ningmai 14 × Yang 12G16 | A |
| Line 109 | Ningmai 14 × Yang 12G16 | A |
| Line 110 | Ningmai 14 × Yang 12G16 | A |
| Line 111 | Ningmai 14 × Yang 12G16 | A |
| Line 112 | Ningmai 14 × Yang 12G16 | A |
| Line 113 | Ningmai 14 × Yang 12G16 | A |
| Line 114 | Ningmai 14 × Yang 12G16 | A |
| Line 115 | Ningmai 14 × Yang 12G16 | A |
| Line 116 | Ningmai 14 × Yang 12G16 | A |
| Line 117 | Ningmai 14 × Yang 12G16 | A |
| Line 118 | Ningmai 24 × Zi 12-6 | A |
| Line 119 | Ningmai 24 × Zi 12-6 | A |
| Line 120 | Ningmai 24 × Zi 12-6 | A |
| Line 121 | Ningmai 24 × Zi 12-6 | A |
| Line 122 | Ningmai 24 × Zi 12-6 | A |
| Line 123 | Ning 09-72 × Zi 12-6 | A |
| Line 124 | Ning 09-72 × Dongmai 1301 | A |
| Line 125 | Ning 09-72 × Dongmai 1301 | A |
| Line 126 | Ning 12046 × Yangjiangmai 580 | A |

TABLE 4-continued

Typing results of wheat materials

| Number | Combination (generation F5) | genotype |
|---|---|---|
| Line 127 | Ning 12046 × Yangjiangmai 580 | A |
| Line 128 | Ning 12046 × Yangjiangmai 580 | A |
| Line 129 | Ning 12046 × Yangjiangmai 580 | A |
| Line 130 | Ning 13134 × Yang 12-145 | A |
| Line 131 | Ning 13134 × Yang 12-145 | A |
| Line 132 | Ning 13134 × Yang 12-145 | A |
| Line 133 | Ning 13199 × Zhenmai 168 | A |
| Line 134 | Ning 13199 × Zhenmai 168 | A |
| Line 135 | Ning 13199 × Zhenmai 168 | A |
| Line 136 | Ning 14271 × Yangmai 9 | A |
| Line 137 | Ning 14271 × Yangmai 9 | A |
| Line 138 | Ning 14271 × Yangmai 9 | A |
| Line 139 | Ning 14271 × Yangmai 9 | A |
| Line 140 | Ning 14271 × Yangmai 9 | A |
| Line 141 | Ning 14271 × Yangmai 9 | A |
| Line 142 | Ning 14271 × Yangmai 9 | A |
| Line 143 | Ning 14271 × Zhenmai 168 | A |
| Line 144 | Ning 14271 × Zhenmai 168 | A |
| Line 145 | Ning 14271 × Zhenmai 168 | A |
| Line 146 | Ning 14271 × Zhenmai 168 | A |
| Line 147 | Ning 14271 × Zhenmai 168 | A |
| Line 148 | Ning 14271 × Zhenmai 168 | A |
| Line 149 | Ning 14271 × Zhenmai 168 | A |
| Line 150 | Ninghong 14103 × Yang 12G16 | A |
| Line 151 | Ninghong 14103 × Yang 12G16 | A |
| Line 152 | Ninghong 14103 × Yang 12G16 | A |
| Line 153 | Yangmai 158 × Zi 12-6 | A |
| Line 154 | Yangmai 16 × Huaimaijian 3 | A |
| Line 155 | Yangmai 16 × Huaimaijian 3 | A |
| Line 156 | Yangmai 20 × Zhen 12096 | A |
| Line 157 | Yangmai 20 × Zhen 12096 | A |
| Line 158 | Yangmai 20 × Zhen 12096 | A |
| Line 159 | Yangmai 20 × Zhen 12096 | A |
| Line 160 | Yangmai 20 × Zhen 12096 | A |
| Line 161 | Yangmai 20 × Zhen 12096 | A |
| Line 162 | Yangmai 20 × Zhen 12096 | A |
| Line 163 | Yangmai 20 × Zhen 12096 | A |
| Line 164 | Yangmai 20 × Zhen 12096 | A |
| Line 165 | Yangmai 20 × Zhen 12096 | A |
| Line 166 | Yangmai 20 × Zhen 12096 | A |
| Line 167 | Yangmai 22 × Nongmai 126 | A |
| Line 168 | Yangmai 22 × Nongmai 126 | A |
| Line 169 | Yangmai 22 × Nongmai 126 | A |
| Line 170 | Yangmai 22 × Nongmai 126 | A |
| Line 171 | Yangmai 22 × Nongmai 126 | A |
| Line 172 | Yangmai 22 × Nongmai 126 | A |
| Line 173 | Yangmai 22 × Nongmai 126 | A |
| Line 174 | Yangmai 22 × Nongmai 126 | A |
| Line 175 | Yangmai 22 × Nongmai 126 | A |
| Line 176 | Yangmai 22 × Nongmai 126 | A |
| Line 177 | Yangmai 22 × Nongmai 126 | A |
| Line 178 | Yangmai 22 × Nongmai 126 | A |
| Line 179 | Yangmai 22 × Nongmai 126 | A |
| Line 180 | Yangmai 22 × Nongmai 126 | A |
| Line 181 | Yangmai 22 × Nongmai 126 | A |
| Line 182 | Yangmai 22 × Nongmai 126 | A |
| Line 183 | Yangmai 22 × Nongmai 126 | A |
| Line 184 | Yangmai 22 × Nongmai 126 | A |
| Line 185 | Yangmai 23 × Dongmai 1301 | A |
| Line 186 | Yangmai 23 × Dongmai 1301 | A |
| Line 187 | Yangmai 23 × Dongmai 1301 | A |
| Line 188 | Yangmai 23 × Dongmai 1301 | A |
| Line 189 | Yangmai 23 × Dongmai 1301 | A |
| Line 190 | Yangmai 23 × Dongmai 1301 | A |
| Line 191 | Yangmai 23 × Dongmai 1301 | A |
| Line 192 | Yangmai 23 × Dongmai 1301 | A |
| Line 193 | Yangmai 23 × Dongmai 1301 | A |
| Line 194 | Yangmai 23 × Dongmai 1301 | A |
| Line 195 | Yangmai 23 × Dongmai 1301 | A |
| Line 196 | Yangmai 25 × Yang 12G16 | A |
| Line 197 | Yangmai 25 × Yang 12G16 | A |
| Line 198 | Yangmai 25 × Yang 12G16 | A |
| Line 199 | Yangmai 25 × Yang 12G16 | A |
| Line 200 | Yangmai 25 × Yang 12G16 | A |
| Line 201 | Yangmai 25 × Yang 12G16 | D |
| Line 202 | Yang 12-145 × Ning 09-72 | A |

TABLE 4-continued

Typing results of wheat materials

| Number | Combination (generation F5) | genotype |
|---|---|---|
| Line 203 | Yang 12-145 × Ning 09-72 | A |
| Line 204 | Yang 12-145 × Ning 09-72 | A |
| Line 205 | Yang 12-145 × Ning 09-72 | D |
| Line 206 | Yang 12-145 × Ning 09-72 | A |
| Line 207 | Yang 12-145 × Ning 09-72 | A |
| Line 208 | Yang 12-145 × Ning 09-72 | A |
| Line 209 | Yang 12-145 × Ning 09-72 | A |
| Line 210 | Yang 12-145 × Ning 09-72 | A |
| Line 211 | Yang 12-145 × Ning 09-72 | A |
| Line 212 | Yang 12-145 × Ning 09-72 | A |
| Line 213 | Yang 12-145 × Ning 09-72 | A |
| Line 214 | Yang 12-145 × Ning 09-72 | A |
| Line 215 | Yang 12G16 × Zhen 12096 | A |
| Line 216 | Yang 12G16 × Zhen 12096 | A |
| Line 217 | Yang 12G16 × Zhen 12096 | A |
| Line 218 | Yang 12G16 × Zhen 12096 | A |
| Line 219 | Yang 12G16 × Zhen 12096 | A |
| Line 220 | Yang 12G16 × Zhen 12096 | A |
| Line 221 | Yang 12G16 × Zhen 12096 | A |
| Line 222 | Yang 12G16 × Zhen 12096 | A |
| Line 223 | Yang 12G16 × Zhen 12096 | A |
| Line 224 | Yang 12G16 × Zhen 12096 | A |
| Line 225 | Yang 12G16 × Zhen 12096 | A |
| Line 226 | Yang 12G16 × Zhen 12096 | A |
| Line 227 | Yang 12G16 × Zhen 12096 | A |
| Line 228 | Yang 12G16 × Zhen 12096 | A |
| Line 229 | Yang 12G16 × Zhen 12096 | A |
| Line 230 | Yang 12G16 × Zhen 12096 | A |
| Line 231 | Yang 12G16 × Zhen 12096 | A |
| Line 232 | Yang 12G16 × Zhen 12096 | A |
| Line 233 | Yang 12G16 × Zhen 12096 | A |
| Line 234 | Yang 14-163 × Jinfeng 15-6 | A |
| Line 235 | Yang 14-163 × Jinfeng 15-6 | A |
| Line 236 | Yang 14-163 × Jinfeng 15-6 | A |
| Line 237 | Yang 14-163 × Jinfeng 15-6 | A |
| Line 238 | Yang 14-163 × Jinfeng 15-6 | A |
| Line 239 | Yangfumai 2149 × Ning 09-72 | A |
| Line 240 | Yangfumai 2149 × Ning 09-72 | A |
| Line 241 | Yangfumai 2149 × Ning 09-72 | A |
| Line 242 | Yangfumai 2149 × Ning 09-72 | A |
| Line 243 | Yangfumai 2049 × Ning 9 Da 44 | A |
| Line 244 | Yangfumai 2049 × Ning 9 Da 44 | A |
| Line 245 | Yangfumai 2049 × Ning 9 Da 44 | A |
| Line 246 | Yangfumai 2049 × Ning 9 Da 44 | A |
| Line 247 | Yangfumai 2049 × Ning 9 Da 44 | A |
| Line 248 | Yangfumai 2049 × Zi14-W464 | A |
| Line 249 | Yangfumai 2049 × Zi14-W464 | A |
| Line 250 | Yangfumai 2049 × Zi14-W464 | A |
| Line 251 | Zhenmai 9 × Zhen 12096 | A |
| Line 252 | Zhenmai 9 × Zhen 12096 | A |
| Line 253 | Zhenmai 11 × Yangmai 24 | A |
| Line 254 | Zhenmai 11 × Yangmai 24 | B |
| Line 255 | Huamai 6 × Jinfeng 15-6 | B |
| Line 256 | Huamai 6 × Jinfeng 15-6 | A |
| Line 257 | Sumai 8号 × Zi 12-6 | A |
| Line 258 | Sumai 8号 × Zi 12-6 | A |
| Line 259 | Zi 12-6 × Ning 09-72 | A |
| Line 260 | Zi 12-6 × Ning 09-72 | A |
| Line 261 | Zi 12-6 × Ning 09-72 | A |
| Line 262 | Zi 12-6 × Ning 09-72 | A |
| Line 263 | Zi 12-6 × Ning 09-72 | A |
| Line 264 | Zi 12-6 × Ning 09-72 | A |
| Line 265 | Zi 12-6 × Ning 09-72 | A |
| Line 266 | Zi 12-6 × Ning 09-72 | A |
| Line 267 | Zi 12-6 × Yangfumai 4 | A |
| Line 268 | Zi 12-6 × Yangfumai 4 | A |
| Line 269 | Zi 12-6 × Yangfumai 4 | A |
| Line 270 | Zi 12-6 × Yangfumai 4 | A |
| Line 271 | Nongfeng 88 × Ning 09-72 | D |
| Line 272 | Nongfeng 88×Ning 09-72 | A |
| Line 273 | Nongfeng 88 × Ning 09-72 | A |
| Line 274 | Nongfeng 88 × Ning 09-72 | A |
| Line 275 | Nongfeng 88 × Yangfumai 5056 | A |
| Line 276 | Nongfeng 88 × Yangfumai 5056 | A |
| Line 277 | Nongfeng 88 × Yangfumai 5056 | A |
| Line 278 | Nongfeng 88 × Yangfumai 5056 | A |

TABLE 4-continued

Typing results of wheat materials

| Number | Combination (generation F5) | genotype |
|---|---|---|
| Line 279 | Nongfeng 88 × Yangfumai 5056 | A |
| Line 280 | Nongfeng 88 × Yangfumai 5056 | A |
| Line 281 | Nongfeng 88 × Yangfumai 5056 | A |
| Line 282 | Nongfeng 88 × Yangfumai 5056 | A |
| Line 283 | Nongfeng 88 × Yangfumai 5056 | A |
| Line 284 | Nongfeng 88 × Zhenmai 9 | A |
| Line 285 | Nongfeng 88 × Zhenmai 9 | A |
| Line 286 | Nongfeng 88 × Zhenmai 9 | A |
| Line 287 | Nongfeng 88 × Zhenmai 9 | A |
| Line 288 | Nongfeng 88 × Zhenmai 9 | A |
| Line 289 | Nongfeng 88 × Zhenmai 9 | A |
| Line 290 | Nongfeng 88 × Zhenmai 12 | A |
| Line 291 | Nongfeng 88 × Zhenmai 12 | A |
| Line 292 | Nongfeng 88 × Zhenmai 12 | A |
| Line 293 | Nongfeng 88 × Zhenmai 12 | A |
| Line 294 | Nongfeng 88 × Zhenmai 12 | A |
| Line 295 | Dongmai 1301 × Ningmai 14 | A |
| Line 296 | Dongmai 1301 × Ningmai 14 | A |
| Line 297 | Dongmai 1301 × Ningmai 14 | A |
| Line 298 | Dongmai 1301 × Ningmai 14 | A |
| Line 299 | Jingfeng 15-6 × Yangmai 9 | A |
| Line 300 | Ning 0076 × Dongmai 1301 | A |
| Line 301 | Ning 0076 × Dongmai 1301 | A |
| Line 302 | Ning 0076 × Dongmai 1301 | B |
| Line 303 | Ning 0076 × Dongmai 1301 | B |
| Line 304 | Guohong 9 × Ning 15283 | B |
| Line 305 | Guohong 9 × Ning 15283 | B |
| Line 306 | Guohong 9 × Ning 15283 | B |
| Line 307 | Guohong 9 × Ning 15283 | B |
| Line 308 | Guohong 9 × Ning 15283 | B |
| Line 309 | Guohong 9 × Ning 15283 | C |
| Line 310 | Guohong 9 × Ning 15283 | B |
| Line 311 | Guohong 9 × Ning 15283 | B |
| Line 312 | Guohong 9 × Ning 15283 | B |
| Line 313 | Guohong 9 × Ning 15283 | B |
| Line 314 | Guohong 9 × Yang 12-145 | A |
| Line 315 | Guohong 9 × Yang 12-145 | A |
| Line 316 | Guohong 9 × Dongmai 1301 | A |
| Line 317 | Guohong 9 × Dongmai 1301 | A |
| Line 318 | Guohong 9 × Dongmai 1301 | A |
| Line 319 | Guohong 9 × Dongmai 1301 | A |
| Line 320 | Guohong 9 × Dongmai 1301 | A |
| Line 321 | Guohong 9 × Dongmai 1301 | A |
| Line 322 | Guohong 9 × Dongmai 1301 | A |
| Line 323 | Guohong 9 × Dongmai 1301 | A |
| Line 324 | Guohong 9 × Dongmai 1301 | A |
| Line 325 | Guohong 9 × Dongmai 1301 | B |
| Line 326 | Guohong 9 × Dongmai 1301 | B |
| Line 327 | Guohong 9 × Dongmai 1301 | A |
| Line 328 | Ning 14017 × Yang 14-52 | A |
| Line 329 | Ning 14017 × Yang 14-52 | A |
| Line 330 | Ning 14017 × Yang 14-52 | A |
| Line 331 | Ningmai 8/NH1212//Zhenmai 9 | A |
| Line 332 | Ningmai 8/NH1212//Zhenmai 9 | A |
| Line 333 | Ningmai 8/NH1212//Zhenmai 9 | A |
| Line 334 | Ningmai 8/NH1212//Zhenmai 9 | A |
| Line 335 | Ningmai 8/NH1212//Zhenmai 9 | A |
| Line 336 | Ningmai 8/NH1212//Zhenmai 9 | A |
| Line 337 | Ningmai 8/Nongfeng 88//Ning 14296 | A |
| Line 338 | Ningmai 8/Nongfeng 88//Ning 14296 | D |
| Line 339 | Ningmai 13/Zhenmai 9//Nannong 15Y19 | B |
| Line 340 | Ningmai 13/Zhenmai 9//Nannong 15Y19 | C |
| Line 341 | Ningmai 13/Zhenmai 9//Nannong 15Y19 | A |
| Line 342 | Ningmai 13/Longmai 28//Zhenmai 9 | C |
| Line 343 | Ningmai 14/Zhenmai 9//Yangfumai 5056 | A |
| Line 344 | Ningmai 14/Zhenmai 9//Yangfumai 5056 | A |
| Line 345 | Ningmai 14/Zhenmai 9//Yangfumai 5056 | A |
| Line 346 | Ningmai 14/Zhenmai 9//Yangfumai 5056 | A |
| Line 347 | Ning 9 Da 44/Yang 12G16//Shengxuan 5 | A |
| Line 348 | Ning 9 Da 44/Yang 12G16//Shengxuan 5 | A |
| Line 349 | Ning 9 Da 44/Yang 12G16//Shengxuan 5 | A |
| Line 350 | Ning 9 Da 44/Yang 12G16//Shengxuan 5 | A |
| Line 351 | Ning 9 Da 44/Yang 12G16//Shengxuan 5 | A |
| Line 352 | Ning 9 Da 44/Yang 12G16//Shengxuan 5 | A |
| Line 353 | Ning 9 Da 44/Yang 12G16//Shengxuan 5 | A |
| Line 354 | Ning 9 Da 44/Yang 12G16//Shengxuan 5 | A |

TABLE 4-continued

Typing results of wheat materials

| Number | Combination (generation F5) | genotype |
|---|---|---|
| Line 355 | Ning 9 Da 44/Yang 12G16//Shengxuan 5 | A |
| Line 356 | Ning 9 Da 44/Nongfeng 88//Zhenmai 9 | B |
| Line 357 | Ning 9 Da 44/Nongfeng 88//Zhenmai 9 | A |
| Line 358 | Ning 9 Da 44/Nongfeng 88//Zhenmai 9 | A |
| Line 359 | Ning 9 Da 44/Nongfeng 88//Zhenmai 9 | A |
| Line 360 | Yangmai 16/Ningmai 9//Annong 1124 | A |

Figure 4:
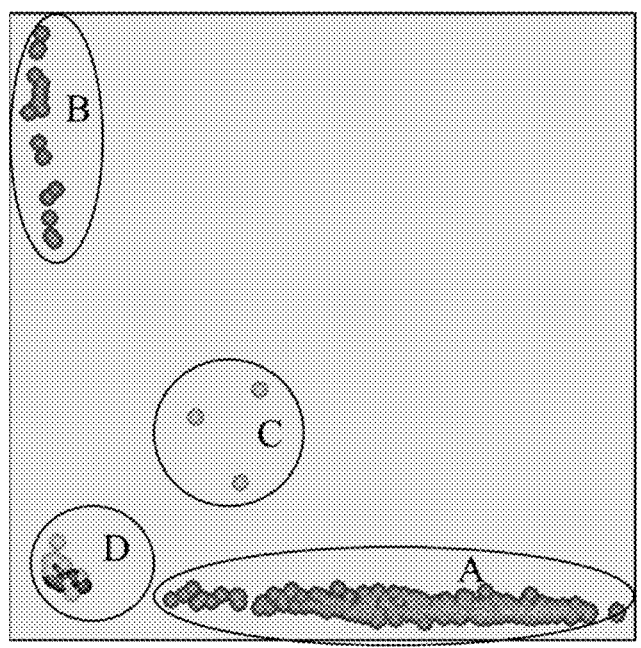
FIG. 4 shows detection results of 360 high-generation lines.

The detection results are shown in FIG. 4. A total of 331 samples of type Rht-B1b/Rht-D1a (blue, A), 18 samples of type Rht-B1a/Rht-D1b (red, B), 3 samples of type Rht-B1b/Rht-D1b (green, C), and 8 samples of type Rht-B1a/Rht-D1a (black, D) were identified in the test. In this detection, only one 384-well plate was used for one amplification reaction, while STS markers needed to be amplified for 4 times, and electrophoresis detection was performed for 4 times. Common KASP markers require double consumables and reagents, so that the multiple KASP labeled P3 can greatly improve efficiency and reduce costs.

What is claimed is:

1. A multiple primer set for Kompetitive Allele Specific PCR (KASP) assay for simultaneously detecting Rht-B1 and Rht-D1 genes controlling wheat plant height, wherein the primer set consists of a forward primer F with a nucleotide sequence consisting of SEQ ID NO. 10, a forward primer H with a nucleotide sequence consisting of SEQ ID NO. 11, and a reverse universal primer R with a nucleotide sequence consisting of SEQ ID NO. 9, wherein the forward primer F comprises a first fluorescent label-binding sequence at its 5' end, and targets a single nucleotide polymorphism (SNP) in the Rht-B1 gene, wherein the forward primer H comprises a second fluorescent label-binding sequence at its 5' end, and targets an SNP in the Rht-D1 gene, wherein the second fluorescent label-binding sequence is different from the first fluorescent label-binding sequence, wherein the reverse universal primer R is shared by the forward primer F and the forward primer H to enable simultaneous PCR amplification from both the Rht-B1 and Rht-D1 genes in a single reaction.

2. A method for simultaneous detection of wheat Rht-B1 and Rht-D1 genotype, wherein the method comprises using the multiple primer set of claim 1; wherein the Rht-B1 genotype is either a Rht-B1a genotype or a Rht-B1b genotype, wherein the Rht-D1 genotype is either a Rht-D1a genotype or a Rht-D1b genotype.

3. The method according to claim 2, wherein the method refers to PCR amplification of wheat samples using the multiple primer set, followed by fluorescence detection performed on the amplified products; if the fluorescence detection result is blue, it indicates that a genotype of the sample wheat is Rht-B1b/Rht-D1a; if the fluorescence detection result is red, it indicates that a genotype of the sample wheat is Rht-B1a/Rht-D1b; if the fluorescence detection result is green, it indicates that a genotype of the sample wheat is Rht-B1b/Rht-D1b; and if the fluorescence detection result is black, it indicates that a genotype of the sample wheat is Rht-B1a/Rht-D1a or blank.

4. The method according to claim 3, wherein the PCR amplification refers to:

PCR reaction system: 0.07 µL of KASP Assay Mix, 2.43 µL of wheat template DNA at a concentration of 20 ng/µL, supplemented with 2×KASP Master Mix to 5 µL, wherein each 100 µL of the KASP Assay Mix comprises: 12 µL of the primer F at a concentration of 100 µM, 12 µL of the primer H at a concentration of 100 µM, and 30 µL of the universal primer R at a concentration of 100 µM, supplemented with ddH$_2$O to 100 µL; and PCR reaction procedure: 94° C. for 15 minutes; 94° C. for 20 s, 61-55° C. for 1 minutes, with a decrease of 0.6° C. per cycle for a total of 10 cycles; 94° C. for 20 s, 55° C. for 1 minutes, a total of 26 cycles.

* * * * *